United States Patent [19]

Hogan

[11] 4,450,862
[45] May 29, 1984

[54] PINCH VALVE ASSEMBLY

[75] Inventor: Thomas H. Hogan, Palo Alto, Calif.

[73] Assignee: Syntex (U.S.A.) Inc., Palo Alto, Calif.

[21] Appl. No.: 234,133

[22] Filed: Feb. 13, 1981

[51] Int. Cl.³ ............................................ F16K 31/126
[52] U.S. Cl. ........................................ 137/595; 251/5; 251/7
[58] Field of Search ........................ 137/595; 251/5, 7

[56] References Cited

U.S. PATENT DOCUMENTS

| 494,984 | 4/1893 | Edmonds | 137/595 X |
|---|---|---|---|
| 1,019,617 | 5/1912 | Everhart | 137/595 X |
| 2,174,965 | 10/1939 | Burdick | 137/595 |
| 2,409,768 | 10/1946 | Lavett | 251/5 X |
| 3,411,540 | 11/1968 | Iannelli | 251/7 X |
| 3,415,276 | 12/1968 | Lind | 251/5 X |
| 3,498,316 | 3/1970 | Pinder | 137/595 |
| 3,550,619 | 12/1970 | Halasz | 137/595 |
| 3,582,284 | 6/1971 | Hamshere | 251/5 X |
| 3,823,724 | 7/1974 | Davis | 251/5 X |
| 4,259,985 | 4/1981 | Bergmann | 137/595 |

FOREIGN PATENT DOCUMENTS 390307 11/1973 U.S.S.R. .................................. 251/5

OTHER PUBLICATIONS

IBM Technical Disclosure Bulletin; vol. 10, No. 4; Published Sep. 1967.

Primary Examiner—Robert G. Nilson
Attorney, Agent, or Firm—David A. Lowin; John A. Dhuey

[57] ABSTRACT

A pinch valve assembly is described for location between the manifold assembly and the flow adjustment valves of a dental handpiece system. The pinch valve assembly of the present invention comprises a housing having a plurality of passageways extending therethrough for receiving a plurality of resilient tubes therein. A plurality of transverse slots extending from each of the passageways to the bottom of the housing are provided and are adapted to receive a plurality of slide elements in each of the slots such that the slide elements can move reciprocally within the slots. The housing is supported on a base and a flexible diaphragm is located between the housing and the base. A rigid disc rests on the diaphragm and supports the slide elements in the slots. A chamber is provided in the base beneath the diaphragm and connected to a source of pressurized fluid. Expansion of the diaphragm forces the rigid disc and the slide elements within their respective slots to move upwardly causing the slide elements to move against the resilient tubing in the passageways in the housing. When the slide elements are pushed against the tubing, the tubing is pinched or crimped against the top section of the housing, thereby shuttng off fluid flow through the resilient tubes. Upon deactivation, the fluid pressure within the chamber in the base is bled off permitting the diaphragm to revert to its rest position, lowering the rigid disc and the slide elements. That movement frees the tubes within the housing such that fluid flow can occur therethrough.

15 Claims, 11 Drawing Figures

PINCH VALVE ASSEMBLY

BACKGROUND OF THE INVENTION

1. Field of the Invention

The present invention is concerned with pinch valve assemblies. In particular, it is concerned with pinch valve assemblies which are particularly useful in controlling the flow of various fluids to a dental handpiece. Fluid flow through a plurality of flexible tubes is controlled with a simple and economical valve of the present invention.

2. State of the Art

Pinch valves have been utilized in the art to accomplish a variety of functions. For example, U.S. Pat. No. 2,590,396 describes a pinch valve having a push pin connected by a lever mechanism to a flexible diaphragm operable according to the pressure existing in a conduit which is passing the fluid to be regulated. A multiple tube and pinch pin assembly to equalize flow through a plurality of flexible tubes is described in U.S. Pat. No. 2,951,495. Blockage of flow in any one or more of the tubes creates an unequal pressure in the manifold chamber to move the pinch valves to selected positions to equalize the pressure and flow in the remaining tubes. A manually operated pneumatically controlled pinch valve for the control of artificial limbs or prosthetic devices by a disabled person is described in U.S. Pat. No. 3,213,882. Pinch valves of the cam-actuated type are described in U.S. Pat. Nos. 3,865,134 and 4,017,974. A relatively recent pinch valve application for controlling fluid flow to dental handpieces is disclosed in U.S. Pat. No. 4,117,861, which utilizes a plurality of resilient metal strips acting as pinch valves in the fluid supply lines to the dental handpiece.

The aforementioned pinch valves typically are relatively complicated and expensive to produce. Accordingly, there is a need for a simple economical pinch valve assembly which can be utilized to control fluid flow through a plurality of flexible tubes. Particularly with respect to dental applications, wherein the utilizable space in a dental operatory is necessarily limited, it is desirable to have a compact and reliable unit for controlling fluid flow, such as air and cooling water, to a dental handpiece.

SUMMARY OF THE INVENTION

A valve assembly is described for controlling fluid flow through a plurality of resilient tubes which comprises a base, a housing attached to the base, the housing having a plurality of passageways extending therethrough for receiving a resilient tube in each of said passageways, the housing further having a slot associated with each of the passageways extending transversely from the passageways to the bottom of the housing, a slide element located in each of the slots for reciprocal movement therein, and actuation means for reciprocally moving the slide elements simultaneously within the slots from a first position, at which fluid flow through the resilient tubes can occur, to a second position, at which fluid flow through the resilient tubes is precluded.

The actuation means can comprise a flexible diaphragm interposed between the housing and the base. Additionally, it is preferred to utilize a rigid disc supported on the diaphragm between the slide elements and the diaphragm upper surface to support the slide elements thereon. The rigid disc assures simultaneous movement of the slide elements with corresponding movement of the diaphragm element.

In another aspect of the invention, two valve assemblies can be stacked base to base or formed with a unitary base to provide a dual assembly for control of fluid flow through a greater plurality of resilient tubes than can be provided with a single assembly.

DETAILED DESCRIPTION OF THE INVENTION

Figure 1:
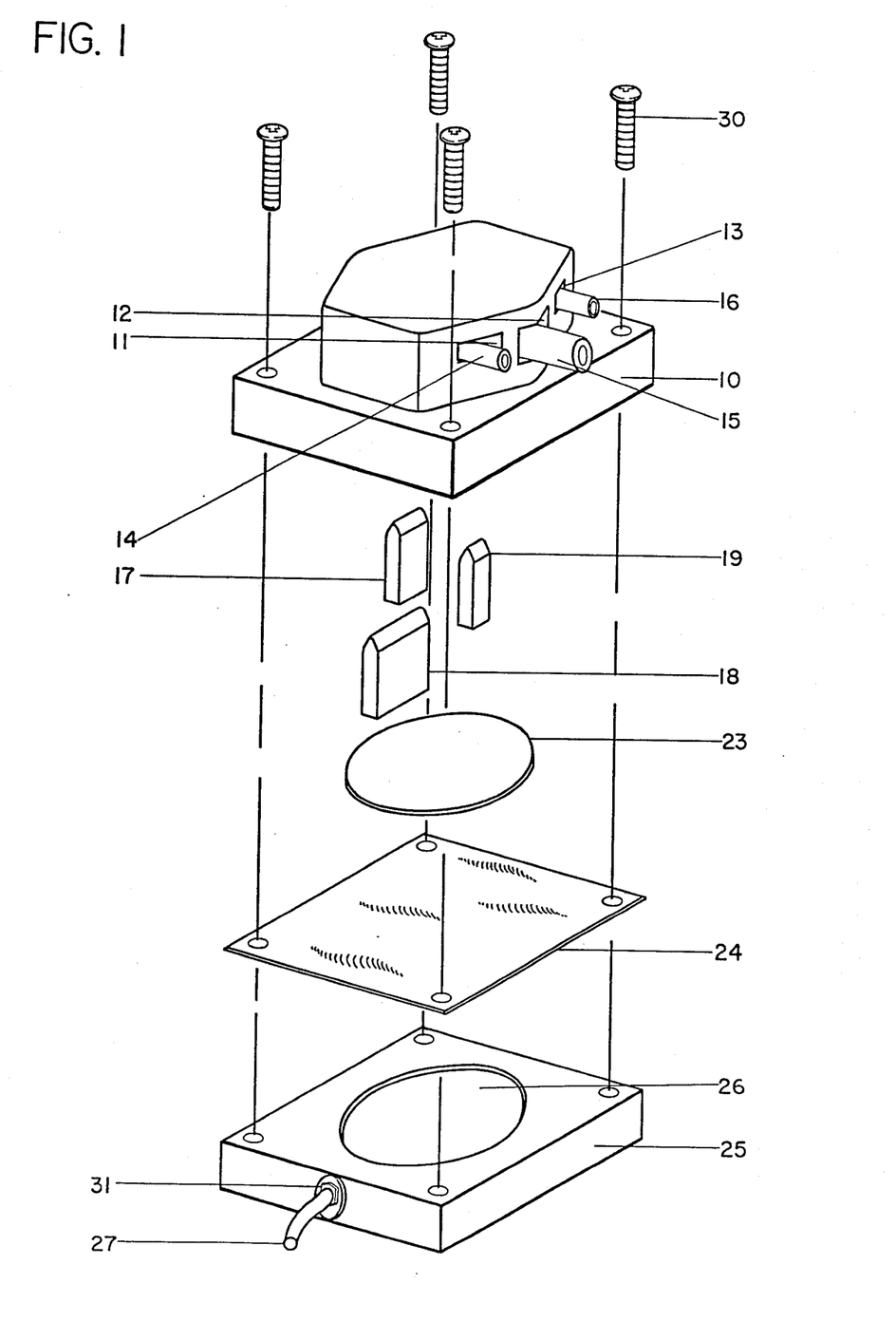
FIG. 1 is an exploded view of the pinch valve assembly of the present invention.
Figure 2:
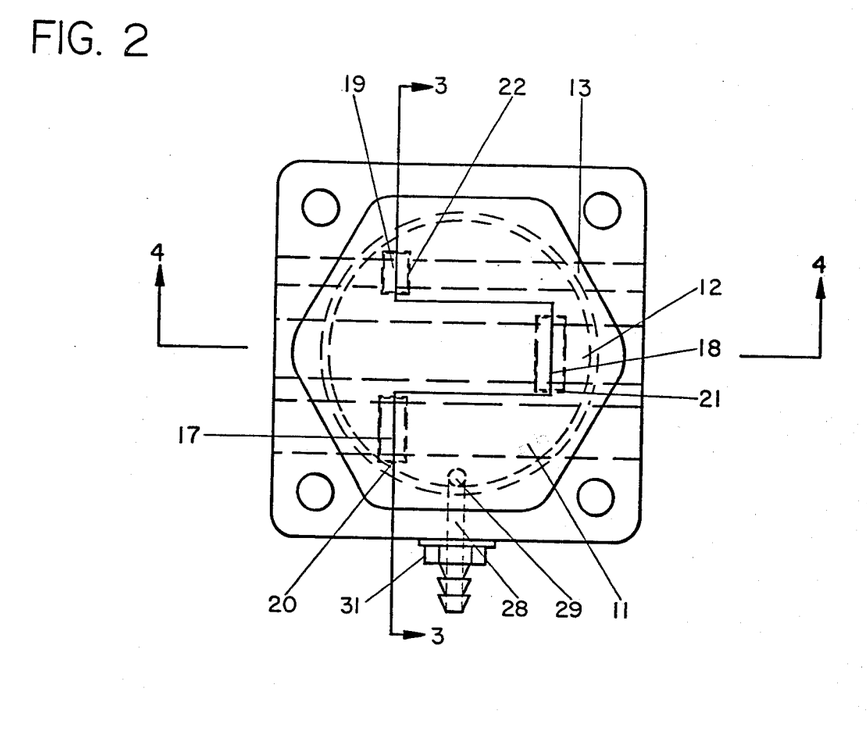
FIG. 2 is a top view of the pinch valve assembly of the present invention utilizing phantom lines to illustrate the relative locations of the various elements of the pinch valve assembly.
Figure 3:
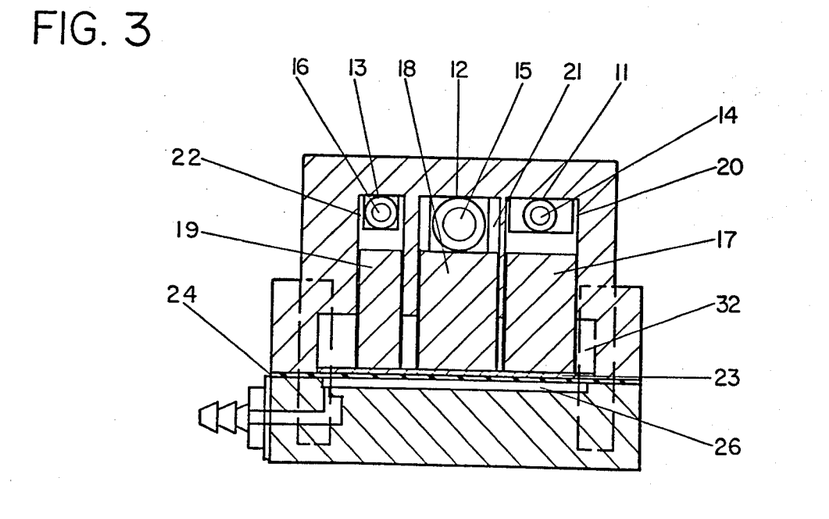
FIG. 3 is a cross-sectional view of the pinch valve assembly along line 3—3 of FIG. 2.

With particular reference to FIGS. 1, 2 and 3 the pinch valve assembly of the present invention comprises a housing 10 supported on a base 25 and secured thereto by screws 30. A plurality of horizontal passageways 11, 12 and 13 are provided in the upper section of housing 10. Each of the passageways 11, 12 and 13 receives a flexible tube 14, 15 and 16, respectively, therein. Beneath each of the passageways and the tubes are rectangular slots 20, 21 and 22 which extend vertically downwardly from the horizontal passageways 11, 12 and 13 through the bottom of housing 10. Reciprocally positioned within slots 20, 21 and 22 are slide elements 17, 18 and 19, respectively.

Between housing 10 and base 25 is interposed a flexible diaphragm 24 which is stretched tautly over a chamber 26 formed in the base 25. Diaphragm 24 is clamped between housing 10 and base 25 when screws 30 are fastened through housing 10 into base 25. A rigid, circular disc 23 is positioned between the upper surface of the diaphragm 24 and the bottom edge of slide elements 17, 18 and 19. A chamber 32 is provided in the lower portion of housing 10 to accommodate movement of rigid disc 23 and diaphragm 24. A connecting passage 28 extends below the chamber 26 in base 25 and is connected to chamber 26 by a vertical bore 29 to supply pressurized air to chamber 26 and the bottom of diaphragm 24. A fitting connector 31 is fastened within connecting passage 28 and is connected to a conduit 27, which is connected to a source of pressurized air.

Figure 4A:
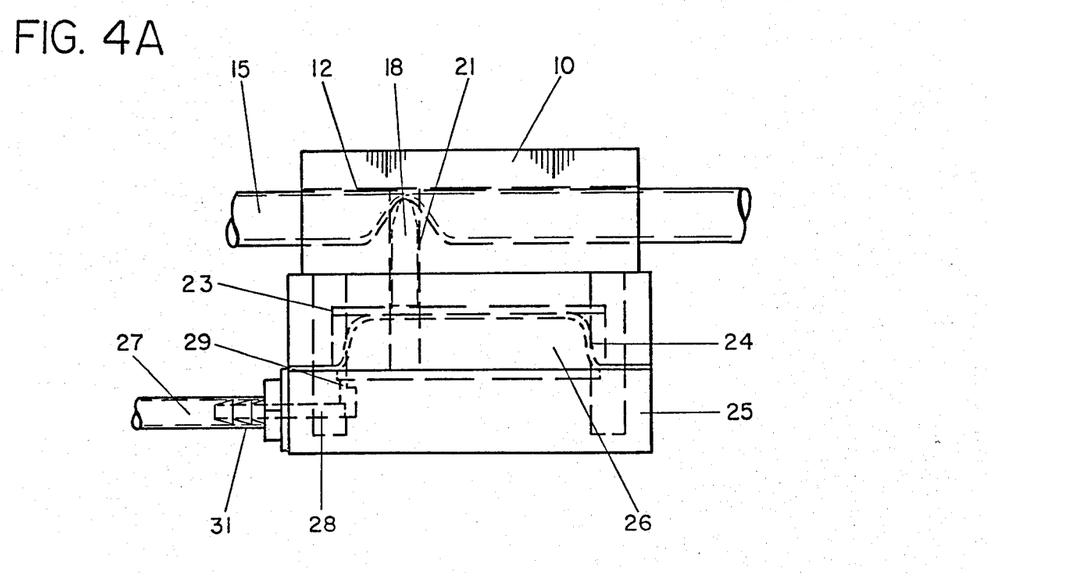
FIG. 4A is a representative cross-sectional view of the pinch valve assembly in a non-flow mode along line 4—4 of FIG. 3.

The pinch valve assembly can be conveniently located between the coolant air manifold, drive air manifold and coolant water manifold and the handpiece in a fluid supply and control system for a dental handpiece or a plurality of dental handpieces. Coolant air, drive air and coolant water are supplied from the respective manifolds through flexible tubes 14, 15 and 16, respectively, to a set of dental handpiece connections. When pressurized air is supplied through conduit 27 into chamber 26 below diaphragm 24, diaphragm 24 and rigid disc 23 are forced toward housing 10 in a manner representatively illustrated in FIG. 4A. In that operative mode, slide element 18 is caused to impinge on and crimp drive air tube 15 between itself and housing 10. That action effectively precludes flow through drive air tube 15. Slide elements 17 and 19 will at the same time crimp their respective tubes 14 and 16 to prevent flow through them as well.

Since it is desired to prevent flow through each of flexible tubes 14, 15 and 16 simultaneously, slide elements 17, 18 and 19 must be appropriately dimensioned such that they will each effectively crimp their respective tubes at the same extent of their travel on rigid disc 23. In applications utilizing conventional flexible polyvinylchloride tubing, it has been found satisfactory to make the slide elements of equal length. However, since tubing of various wall thicknesses and resiliency may be utilized for fluid supply to the handpieces, adjustments on the lengths of the slide elements may have to be made. Such adjustments are considered readily apparent to one skilled in the art.

Figure 4B:
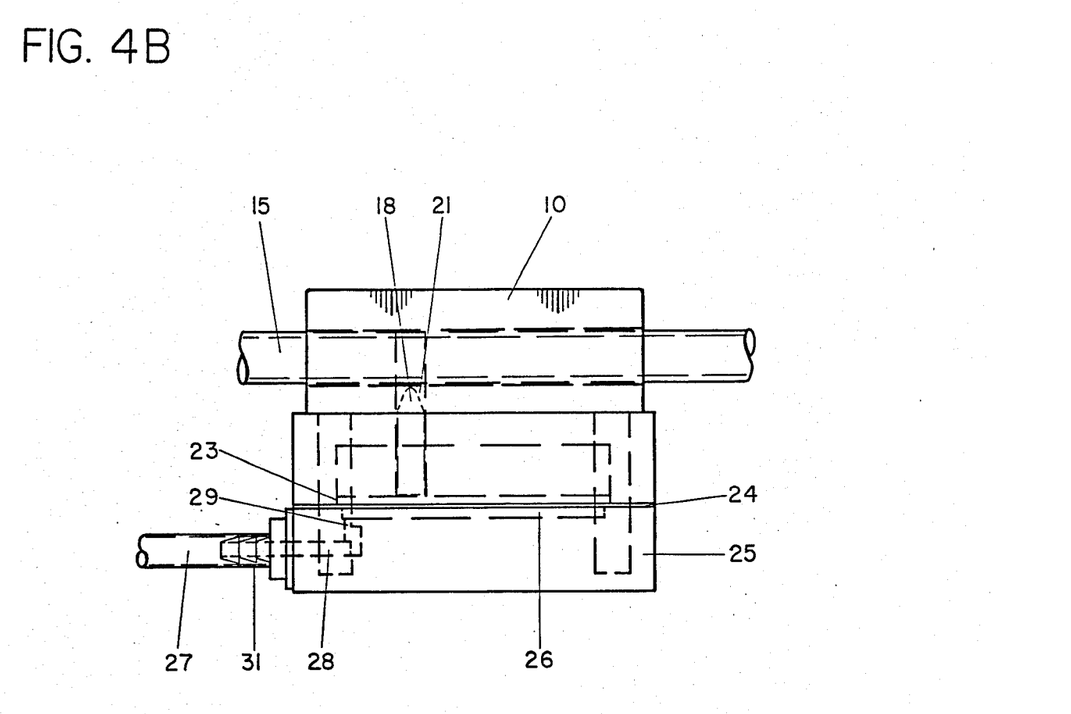
FIG. 4B is a representative cross-sectional view of the pinch valve assembly in a flow mode along line 4—4 of FIG. 3.

When pressurized air is released from chamber 26, diaphragm 24 assumes a relaxed position as illustrated in FIG. 4B. Forces urging the slide elements into contact with their respective tubes are removed and the tubing expands to permit fluid flow therethrough. The resilient nature of the tubes biases the slide elements toward the bottom of the housing to a position at which flow through the tubes can occur. Other biasing means, such as a spring interposed between each slide element and the housing, could be used as well. FIG. 4B illustrates the configuration adopted by that portion of the pinch valve assembly relating to drive air line 15 in the flow mode. In that operational mode, tubes 14 and 16 and slide elements 17 and 19 will behave similarly and flow of coolant air, drive air coolant water to a handpiece can take place. A more detailed description of an associated supply and control system for a plurality of dental handpieces is set forth below.

Slide elements 17, 18 and 19 are desirably manufactured with a slight taper near the end of the slide elements which contact the resilient tubes. Tapering maximizes the crimping force applied at the area of contact with the flexible tubing and assures positive cut off of flow through the flexible tubing.

Figure 5:
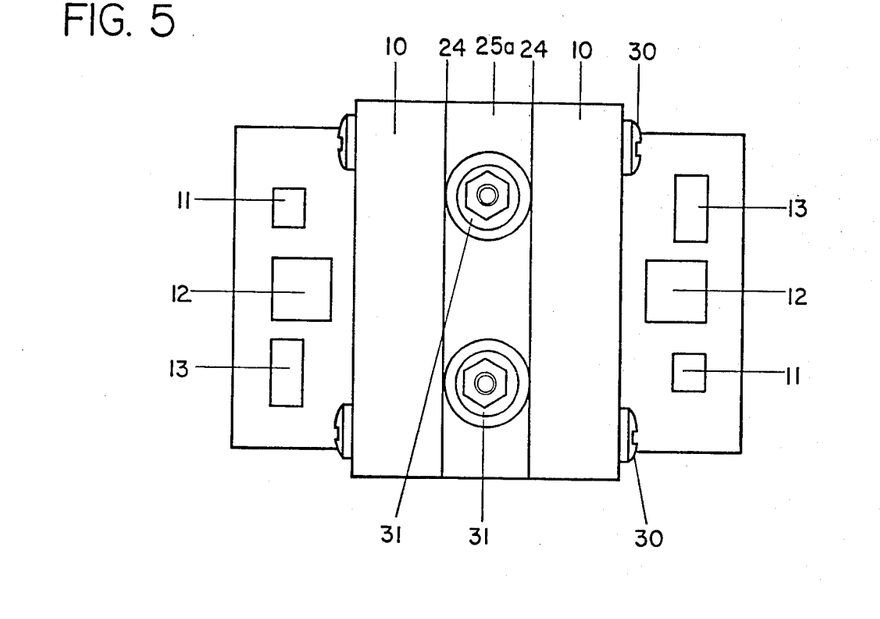
FIG. 5 is a front, elevational view of the dual assembly of the present invention.
Figure 6:
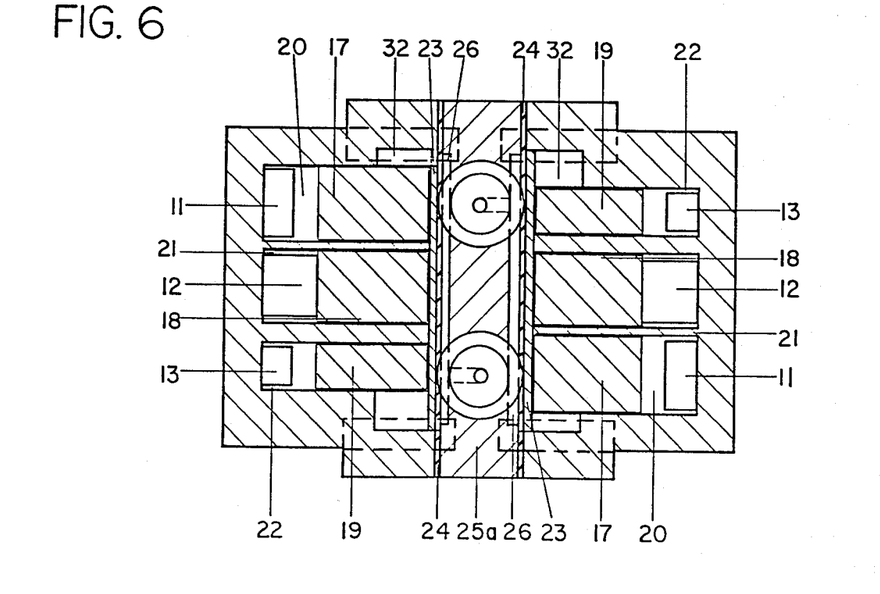
FIG. 6 is a cross-sectional view of the dual assembly of FIG. 5.

A further aspect of the present invention relates to a dual assembly pinch valve illustrated in FIGS. 5 and 6 wherein like numerals refer to similar components as described previously. Such a pinch valve assembly utilizes a base 25a having chambers 26 formed on opposed faces thereof. Each of the chambers 26 is in fluid communication with tubing connectors 31 in a like manner as described with the single valve assembly. Diaphragms 24 are secured between opposed faces of base 25a and housings 10. Rigid discs 23, movable in chambers 32, are provided between diaphragms 24 and slide elements 17, 18 and 19, which are adapted to reciprocate in slots 20, 21 and 22 as described previously. Passageways 11, 12 and 13 are adapted to receive flexible tubes carrying cooling air, drive air and coolant water to two dental handpieces. Each of the single pinch valve assemblies comprising the dual assembly can be operated independently, or if supplied with actuation air simultaneously could be operated in unison.

Figure 7A:
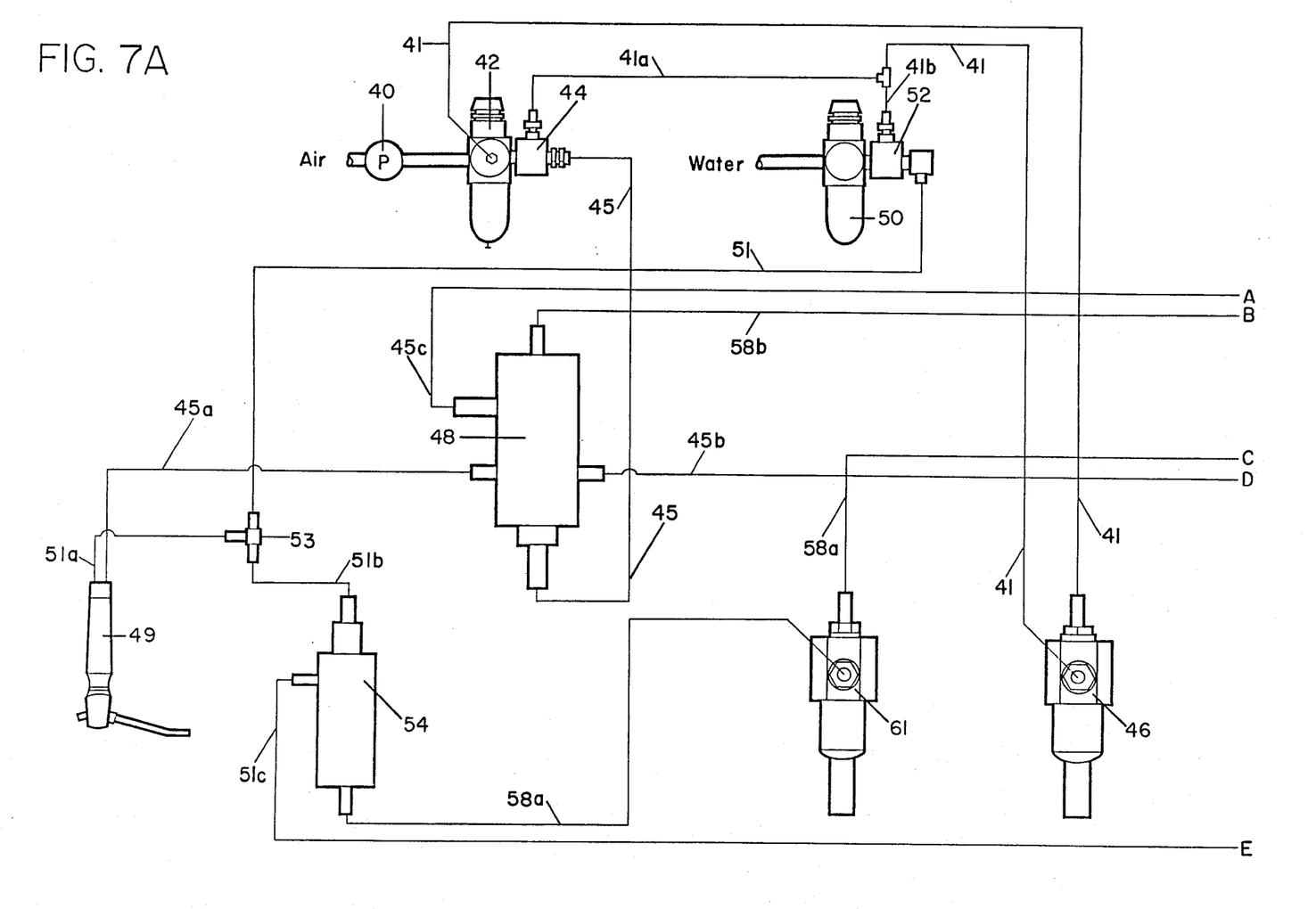
FIGS. 7A, 7B and 7C taken together are a schematic flow diagram for a control and supply system for a multiple handpiece system utilizing the present invention.
Figure 7B:
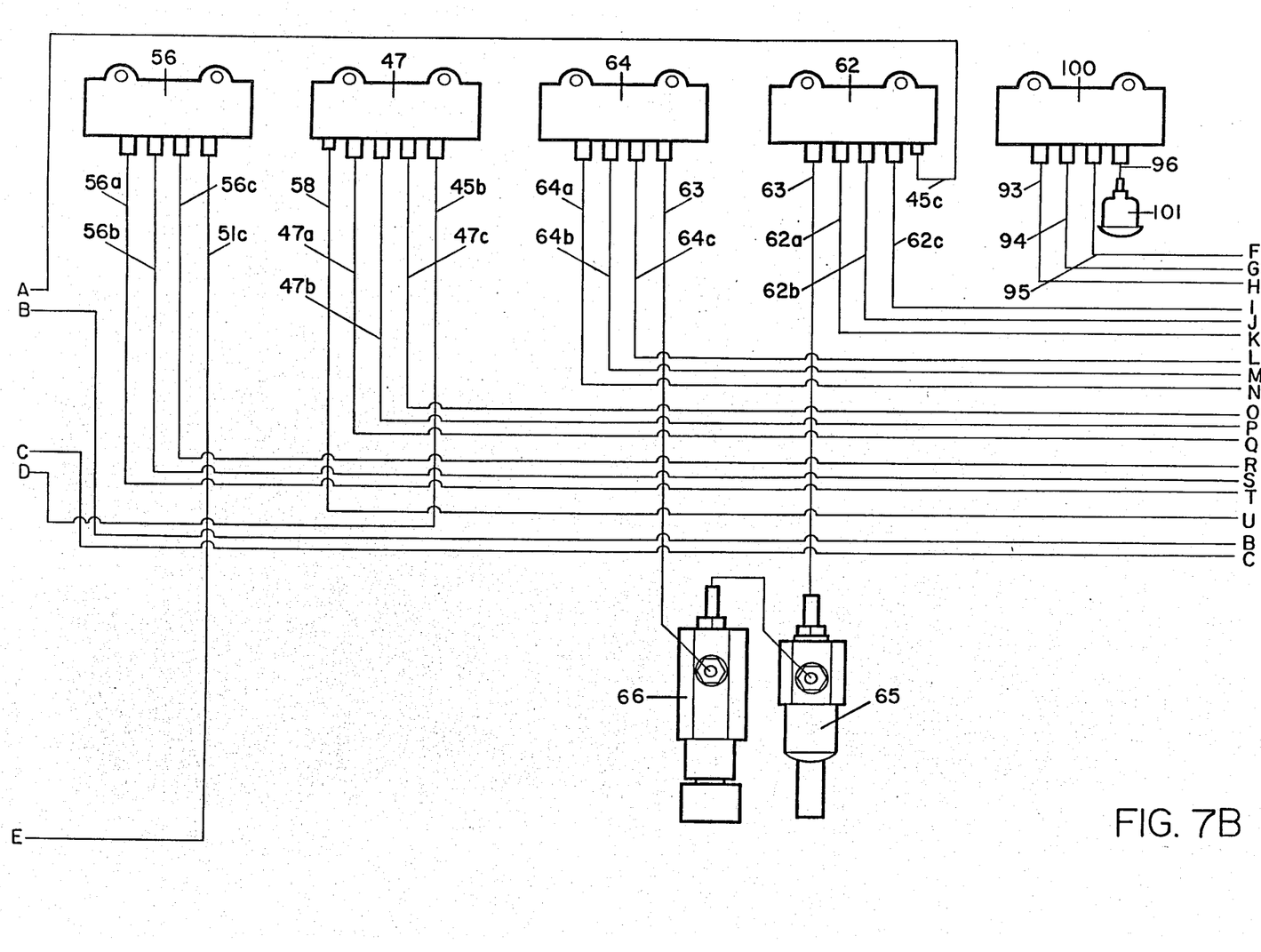
Figure 7C:
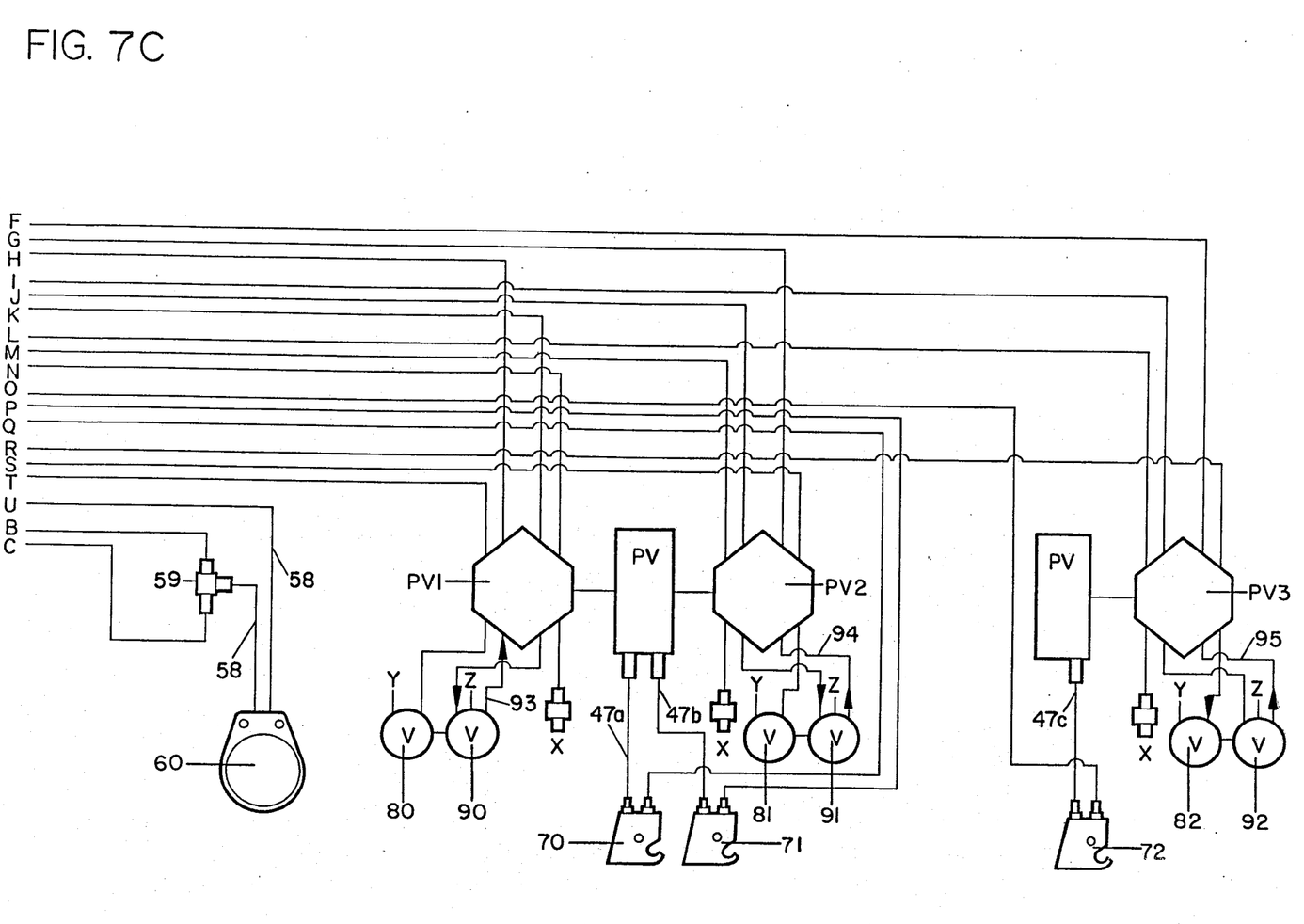

The pinch valve assembly of the present invention is conveniently located between the coolant air manifold, drive air manifold and coolant water manifold and the handpiece connections in a control assembly for a plurality of dental handpieces. A schematic of a control assembly for three handpieces is illustrated in FIGS. 7A, 7B and 7C. Modifications of that assembly for control of fewer or more than three handpieces will be readily apparent to those skilled in the dental field.

As illustrated in FIG. 7, compressed air is supplied to the control assembly from a pump or compressor 40 through a regulator 42. Regulator 42 reduces the line pressure to about 80 psi which has been found satisfactory for usual operation. The supply air is directed through an air supply master valve 44 to supply line 45 which ultimately provides supply air to air supply manifold 47. Air supply master valve 44 is air actuated and controlled by a master valve 46 which is supplied with actuation air via line 41 which extends from regulator 42 at the upstream side of air supply master valve 44. Line 41 is bifurcated into a line 41a, which supplies actuation air to air supply master valve 44, and a line 41b, which supplies actuation air to a water supply master valve 52, the operation of which will be described hereinafter.

Air supply line 45 provides supply air through an air control block 48 to air supply manifold 47 via line 45b. A subsidiary air supply line 45a extends from air control block 48 to a syringe 49. Air flow through control block 48 through lines 45a and 45b is uninterupted as no valving is provided by air control block 48 for those lines, as can be seen from FIG. 8.

Coolant water is supplied to the system from an office main line through regulator 50, which typically provides coolant water at about 40 psi. A water supply master valve 52 is provided on the outlet side of regulator 50 and controlled via lines 41 and 41b by master valve 46. Coolant water flows via line 51 from water supply master valve 52 to a T-connector 53 and into water control block 54 through line 51b. Line 51a provides coolant water from T-connector 53 to syringe 49. Separate air and water control valves are provided in syringe 49 for the ultimate control of air and water therefrom.

Water control block 54 provides an air-actuated valving action for the coolant water flowing through lines 51b and 51c. A satisfactory control block is an air-actuated water control valve sold by Clippard Minimatic of Cincinnati, Ohio. Other conventional air actuated control valves could be used as well. Coolant water line 51c extends from the outlet of water control block 54 and ultimately to coolant water manifold 56.

An air supply air line 58 extends from air supply manifold 47 to a foot control 60 which provides for an on-off control of air flowing in line 58. From foot control 60, air line 58 extends to a T-connector 59 and ultimately to air control block 48 to provide actuation air thereto. Air line 58a extends from T-connector 59 through an on-off valve 61 to water control block 54 to provide actuation air thereto, as will be described more fully hereinafter.

Air line 45c extends from air control control block 48 to drive air manifold 62. An air outlet line 63 extends from drive air manifold 62 through an on-off coolant air valve 65 and a coolant air flow adjustment valve 66 to coolant air manifold 64.

Three handpieces (not shown) are supplied with coolant air, coolant water and air drive via connections X, Y and Z, respectively, from the coolant air manifold, coolant water manifold and air drive manifold through flexible supply tubes passing through pinch valves PV1, PV2 and PV3 of the present invention. Handpiece holders 70, 71 and 72 are provided for supporting the handpieces on a console (not shown). Each of handpiece holders 70, 71 and 72 is conventionally provided with a valve which is opened by insertion of handpiece in the handpiece holder or closed by removal of the handpiece from the handpiece holder.

Supply air from air supply manifold 47 is provided to handpiece holders 70, 71 and 72 via air lines 47a, 47b and 47c, respectively.

The outlet lines 47a, 47b and 47c from the handpiece holders 70, 71 and 72, respectively, provide supply air to pinch valves PV1, PV2 and PV3. Each of the lines 47a, 47b and 47c is in fluid communication with a chamber 26 of the representative pinch valves described in FIGS. 1-6.

Coolant air is supplied to each handpiece at connections X from coolant air manifold 64 via coolant air supply lines 64a, 64b and 64c which pass through pinch valve PV1, PV2 and PV3, respectively. Coolant air is supplied to each handpiece at connections Y from coolant water manifold 56 through supply lines 56a, 56b and 56c which pass through pinch valves PV1, PV2 and PV3, respectively. Water flow control valves 80, 81 and 82 are provided between pinch valves PV1, PV2 and PV3, respectively and connections Y to permit adjustment of coolant water flow to each handpiece. Drive air is supplied to each handpiece at connections Z from drive air manifold 62 via drive air supply lines 62a, 62b and 62c, which pass through pinch valves PV1, PV2 and PV3, respectively. Drive air control valves 90, 91 and 92 are provided between pinch valves PV1, PV2 and PV3, respectively, and connections Z to permit adjustment of drive air flow to each handpiece.

Gage air lines 93, 94 and 95 extend from air control valves 90, 91 and 92, respectively, to gage air manifold 100 to monitor the drive air pressure to the handpieces. A pressure gage 101 is connected via line 96 to gage air manifold 100 for visual indication of the drive air pressure. Gage air lines 93, 94 and 95 are conveniently routed through pinch valves PV1, PV2 and PV3, respectively, so that an indication of drive air pressure is displayed only when a pinch valve is in a flow configuration.

In operation, when the handpieces are placed in their respective handpiece holders, the valves in the handpiece holders are opened and pressurized air flows through handpiece holders 70, 71 and 72 via lines 47a, 47b and 47c to the respective pinch valves PV1, PV2 and PV3. Each of lines 47a, 47b and 47c is the equivalent of conduit 27 described previously. In this mode, pressurized air flows through conduit 27 into chamber 26, as seen most clearly in FIG. 1, of each of the pinch valves to pinch off or crimp representative flexible tubes 14, 15 and 16 in a manner depicted in FIG. 4A. Accordingly, when the handpieces are in their respective handpiece holders, no flow through the pinch valves is permitted, even if foot control 60 is actuated.

When a handpiece is removed from its respective handpiece holder, the valve in the handpiece holder closes and prevents pressurized air from reaching chamber 26 of the pinch valve controlling flow to that handpiece. Air within chamber 26 is bled off through a bleed orifice in the handpiece holder. When the pressure on diaphragm 24 is released, diaphragm 24 assumes a relaxed configuration in a manner as shown in FIG. 4B and flexible tubes 14, 15 and 16 open for fluid flow therethrough.

It is apparent that only the pinch valve in fluid communication with a handpiece holder from which a handpiece has been removed will be placed in a flow configuration. The remaining pinch valves will be closed as long as the other handpieces remain in their respective handpiece holders.

The commencement of fluid flow through a handpiece is dependent on actuation of foot control 60 to provide actuation air to air control block 48 and water control block 54 via lines 58b and 58a, respectively. Air control block 48 contains an air operated valve which when actuated by operation of foot control 60 through line 58b places line 45c in fluid communication with air supply line 45 to provide air to drive air manifold 47 and subsequently to the handpiece via connection Z.

Figure 8:
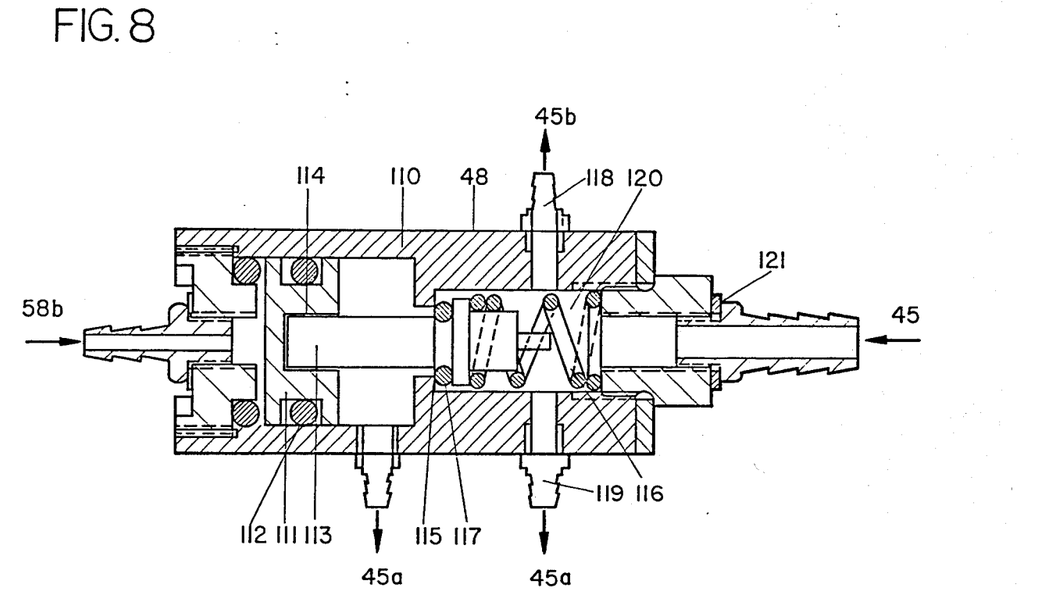
FIG. 8 is a cross-sectional view of an air control block utilized with the control system.

The operation of air control block 48 can be seen most clearly from FIG. 8. As shown, air control block 48 is basically an air-operated valve having a body 110 in which is disposed a piston 111 slidably sealed within body 110 by O-ring 112. A valve stem 113 is longitudinally disposed within body 110 and a central bore 114 provided in piston 111. Valve stem 113 is sealed against valve seat 115 provided on body 110 by the action of spring 116 and O-ring 117. Tubing connectors 118 and 119 are in fluid communication with bore 120 in valve body 110 on the upstream side of valve seat 115. Bore 120 is connected to pressurized supply air and supply air line 45 via connector 121. It is apparent that the only valving action provided by air control block 48 is between lines 45 and 45c. When pressurized air is applied to piston 111 via line 58b, piston 111 forces valve stem 113 away from valve seat 115 and permits the flow of supply air from line 45 through bore 120 into line 45c to drive air manifold 62. Upon release of pressure in line 58b, spring 116 urges valve stem 113 against valve seat 115 to cut off air flow to line 45c. Supply of drive air to drive air manifold 62 also supplies coolant air to coolant air manifold 64 via air line 63 when on-off coolant air valve 65 is in its on position and subsequently to a handpiece connection X. When coolant water on-off valve 61 is in the on position, actuation of foot control 60 activates an air operated valve in water control block 54 via air line 58a, placing coolant water line 51b in fluid communication with coolant water line 51c, to provide coolant water to coolant water manifold 56 via line 51c and eventually to a handpiece connection Y. Accordingly, when a handpiece is removed from a handpiece holder and foot control 60 is actuated, coolant air, drive air and coolant water are supplied to the handpiece. By selectively utilizing on-off valves 61 and 65, it is apparent that the handpiece may be supplied only with coolant air and drive air, only with coolant water and drive air or only with drive air.

A distinct advantage of the pinch valve of the present invention is that it can be located very close to the handpiece and supplied with air from the air supply line with minimal tubing lengths to minimize undesirable pressure losses. Previously, drive air was supplied through foot control 60 which was located on the floor near the dental chair. Substantial tubing length was requied to supply drive air from the foot control to the handpiece which was located above the patient and the dental chair. In the present control system, air passes through foot control 60 only to actuate the air-operated valves in air control block 48 and water control block 54. Neither drive air, coolant air nor coolant water pass directly through foot control 60 and thus supply tubing lengths are kept to a minimum.

While the invention has been described with reference to the specific embodiments thereof, it should be understood by those skilled in the art that various changes can be made and equivalents may be substituted without departing from the true spirit and scope of the invention. All such modifications are intended to be within the scope of the claims appended hereto.

What is claimed is:

1. A valve assembly for controlling fluid flow through a plurality of resilient tubes comprising:
   a base;
   a housing attached to said base, said housing having a plurality of passageways extending therethrough for receiving a resilient tube in each of said passageways, said housing further having a slot associated with each of said passageways extending transversely from said passageways toward the bottom of said housing:
   a plurality of slide elements, a said slide element located in each of said slots for reciprocal movement therein independent of said other slide elements; and
   a single actuation means for reciprocally moving said slide elements, simultaneously within said slots from a first position, at which fluid flow through the resilients tubes can occur, to a second position, at which fluid flow through the resilient tubes is precluded.

2. The valve assembly of claim 1 wherein said actuation means comprises a flexible diaphragm between said housing and said base.

3. The valve assembly as in claim 2 further comprising a rigid disc interposed between said diaphragm and said slide elements, said disc supporting said elements thereon and being movable with said diaphragm.

4. The valve assembly of claim 1 adapted for controlling fluid flow through a plurality of resilient tubes of different diameters and resilience, wherein each said slide element corresponds to one of said resilient tubes and is appropriately dimensioned to control the flow of fluid through said corresponding tube upon operation of said actuation means.

5. The valve assembly of claim 1 comprising biasing means, said biasing means comprising the resilient tubes, whereby the expansion of said resilient tubes to permit fluid flow therethrough biases said slide elements toward said first position.

6. A valve assembly for controlling fluid flow through a plurality of resilient tubes comprising, in combination:
   a base;
   a housing supported on and attached to said base, said housing having a plurality of passageways extending therethrough for receiving a resilient tube in each of said passageways, said housing further having a slot associated with each of said passageways extending transversely from said passageways toward the bottom of said housing;
   a plurality of slide elements, a said slide element located in each of said slots for reciprocal movement therein independent of said other slide elements;
   a single actuation means for reciprocally moving said slide elements, simultaneously within said slots from a first position, at which fluid flow through the resilient tubes can occur, to a second position, at which fluid flow through the resilient tubes is precluded; and
   biasing means for urging said slide elements toward said first position.

7. The valve assembly of claim 6 wherein said actuation means comprises a flexible diaphragm between said housing and said base.

8. The valve assembly of claim 7 further comprising a rigid disc interposed between said diaphragm and said slide elements, said disc supporting said slide elements thereon and being movable with said diaphragm.

9. The valve assembly of claim 6 adapted for controlling fluid flow through a plurality of resilient tubes of different diameters and resilience, wherein each said slide element corresponds to one of said resilient tubes and is appropriately dimensioned to control the flow of fluid through said corresponding tube upon operation of said actuation means.

10. The valve assembly of claim 6 wherein said biasing means comprises the resilient tubes, whereby the expansion of said resilient tubes to permit fluid flow therethrough biases said slide elements toward said first position.

11. A valve assembly for controlling fluid flow through a plurality of resilient tubes comprising:
    a base;
    a pair of housings attached to opposed sides of said base, each of said pair of housings having a plurality of passageways extending therethrough for receiving a resilient tube in each of said passageways, said housings further having a slot associated with each of said passageways extending transversely from said passageways toward the bottom of said housings;
    a plurality of slide elements, a said slide element located in each of said slots for reciprocal movement therein independent of said other slide elements; and
    actuation means for reciprocally moving said slide elements, simultaneously within said slots from a first position, at which fluid flow through the resilient tubes can occur, to a second position at which fluid flow through the resilient tubes is precluded.

12. The valve assembly of claim 11 adapted for controlling fluid flow through a plurality of resilient tubes of different diameters and resilience, wherein each said slide element corresponds to one of said resilient tubes and is appropriately dimensioned to control the flow of fluid through said corresponding tube upon operation of said actuation means.

13. The valve assembly of claim 11 comprising biasing means, said biasing means comprising the resilient tubes, whereby the expansion of said resilient tubes to permit fluid flow therethrough biases said slide elements toward said first position.

14. A valve assembly for controlling fluid flow through a plurality of resilient tubes comprising:
    a base;
    a pair of housings attached to opposed sides of said base, each of said pair of housings having a plurality of passageways extending therethrough for receiving a resilient tube in each of said passageways, said housings further having a slot associated with each of said passageways extending transversely from said passageways toward the bottom of said housings;

a slide element located in each of said slots for reciprocal movement therein; and actuation means for reciprocally moving said slide elements simultaneously within said slots from a first position, at which fluid flow through the resilient tubes can occur, to a second position at which fluid flow through the resilient tubes is precluded, said actuation means comprising a flexible diaphragm between each of said housings and said base.

15. The valve assembly of claim 14 further comprising a rigid disc interposed between each of said diaphragms and said slide elements, said disc supporting said elements thereon and being movable with said diaphragm.

* * * * *